(12) United States Patent
Morgan

(10) Patent No.: US 7,332,344 B2
(45) Date of Patent: Feb. 19, 2008

(54) LUMINESCENCE ASSAYS

(75) Inventor: Christopher G. Morgan, Manchester (GB)

(73) Assignee: Photonic Research Systems Limited (GB)

( * ) Notice: Subject to any disclaimer, the term of this patent is extended or adjusted under 35 U.S.C. 154(b) by 898 days.

(21) Appl. No.: 10/086,213

(22) Filed: Feb. 28, 2002

(65) Prior Publication Data

US 2002/0119485 A1   Aug. 29, 2002

Related U.S. Application Data

(63) Continuation-in-part of application No. 09/381,838, filed on Dec. 1, 1999, now abandoned.

(51) Int. Cl.
*G01N 21/76* (2006.01)
(52) U.S. Cl. ............... 436/172; 436/56; 436/81; 436/517; 436/518; 436/523; 436/524; 436/525; 436/527; 436/533; 436/537; 435/7.1; 435/968; 435/7.92; 422/82.05; 422/82.08
(58) Field of Classification Search ............... 436/56, 436/63, 81, 518, 523–535, 164, 172, 517, 436/537; 422/82.05, 82.08, 82.09; 356/244, 356/346; 435/968, 973, 7.92–7.95, 7.1
See application file for complete search history.

(56) References Cited

U.S. PATENT DOCUMENTS

| | | | |
|---|---|---|---|
| 5,156,972 A | 10/1992 | Issachar | |
| 5,399,315 A | 3/1995 | Paz-Pujalt | |
| 5,622,821 A | * 4/1997 | Selvin et al. | 435/6 |
| 5,736,410 A | * 4/1998 | Zarling et al. | 436/172 |
| 5,830,769 A | 11/1998 | Wieder et al. | |
| 6,159,686 A | 12/2000 | Kardos et al. | |

FOREIGN PATENT DOCUMENTS

| | | |
|---|---|---|
| WO | WO 9407142 A | 3/1994 |
| WO | WO 9627798 A | 9/1996 |

* cited by examiner

*Primary Examiner*—Gailene R. Gabel
(74) *Attorney, Agent, or Firm*—Woodard, Emhardt, Moriarty, McNett & Henry LLP

(57) ABSTRACT

A method of detecting an analyte is described in which an up-converting luminescent species that is excited by absorption of long wavelength light is provided as a donor of energy to an acceptor species that can be bound to, or generated in proximity to, the luminescent species. The analyte either alters the proximity between the luminescent species and the acceptor species or alters the absorbance or luminescence properties of the acceptor species. The luminescent energy donor is excited with long wavelength light and transfers up-converted energy to the proximate acceptor species and this transfer of energy is detected by measurement of appropriate luminescence properties of either the donor or of the acceptor or both.

26 Claims, 4 Drawing Sheets

LUMINESCENCE ASSAYS

CROSS-REFERENCE TO RELATED APPLICATIONS

This application is a continuation-in-part of application Ser. No. 09/381,838, filed on Dec. 1, 1999, now abandoned.

BACKGROUND OF THE INVENTION

The present invention relates to luminescence assays based on transfer of excitation energy from a donor species to an acceptor species.

The present invention relates to luminescence assays based on transfer of excitation energy from a donor species to an acceptor species.

Fluorescence, phosphorescence and related technologies (herein referred to as "luminescence" to include in this context all processes where energy is emitted subsequent to an excitation process triggered by absorption of electromagnetic radiation) are now widely used in a variety of analytical schemes. Luminescent materials are used as tracers on the basis of the high detection sensitivity that can be achieved, but are also used as environmentally responsive "probes" to monitor local conditions, such as pH, ion concentrations, oxygen tension etc. Luminescent species can also be used to detect and sometimes quantify the proximity of an agent which is able to modify the emission process on close approach or contact.

It is well known that energy can be transferred by a variety of means from an excited species (the "donor") to a second species able to act as an energy acceptor. One of the most common examples of such transfer involves a radiationless process known as resonance energy transfer, the efficiency of which usually has an inverse sixth power dependence on distance between donor and acceptor. Distance-dependent energy transfer between donor and acceptor species has been used in a variety of analytical and assay formats. An analyte might be detected on the basis of its ability to bind to a site where it can function as one member of the energy transfer donor-acceptor pair. Alternatively, the assay might be conducted in a competitive format where the analyte displaces a labelled analogue from a site and the displacement can be detected and quantified by changes in energy transfer between the site and the analogue. One common type of assay involves the detection of an analyte on the basis of its ability to bind two recognition molecules such as antibodies simultaneously. In this "sandwich" format, the proximity of the two bound species can be determined by energy transfer between labels bound to the antibodies. A recent example of an energy transfer assay using a luminescent cryptate of long emissive lifetime to transfer energy to a short-lived acceptor species is given by G. Mathis ("Rare Earth Cryptates and Homogeneous Fluoroimmunoassays with Human Sera", Clinical Chemistry, Volume 39(9), 1953-1959, (1993)).

Another approach to the assay of enzymes or similar catalytic species (e.g. ribozymes) relies on the ability of the analyte to cleave a chemical bond linking an energy transfer donor to an acceptor species. For example, a protease can be assayed by monitoring the decrease in energy transfer efficiency between donor and acceptor linked together by a peptide fragment. As the linkage is broken the donor and acceptor become separated and efficient transfer of energy is no longer possible. Conversely, an analyte able to initiate chemical bond formation might be assayed on the basis of increase in energy transfer between a suitable donor and acceptor pair as they become linked together. These and similar methods of assay based on transfer of excitation energy are well known in the literature.

For a general discussion of analytical applications of luminescence in Biology see for example "Applications of Luminescence Spectroscopy to Quantitative Analyses in Clinical and Biological Samples", P. Froehlich in "Modem Fluorescence Spectroscopy" Volume 2, E. L. Wehry ed., Plenum, N.Y. (1976). Details of a variety of fluorescence assay procedures are given in "Principles and Practice of Fluoroimmunoassay Procedures", D. S. Smith, M. Hassan and R. D. Nargessi in Volume 3 of the same series.

Most assays involving energy transfer processes are relatively insensitive and can have limited dynamic range. One problem with all luminescence detection is the sensitivity limit set by background. In this context, background might be unwanted luminescence from sample or container, elastically or inelastically scattered exciting light which is not totally rejected by optical filters, luminescence from filters themselves or from other optical elements or any other source of electromagnetic radiation detectable by the measuring apparatus. In absence of background, luminescence methods are commonly able to detect single atoms or molecules. Most analytical luminescence measurements fall short of this sensitivity by orders of magnitude and therefore methods to minimise background are very important in practical applications. Unfortunately, luminescence energy transfer is commonly troubled by background from a variety of causes.

In a practical measurement of energy transfer, ideally the donor is excited by radiation not absorbed by the acceptor. The transfer is detected either by measurement of quenching of donor emission (or related parameters such as change in donor decay rate), or by the sensitised emission from the acceptor if this is also luminescent. Ideal conditions are rarely achieved however and the following potential difficulties and sources of background must be considered:

It is often difficult to avoid some level of direct excitation of the acceptor species by radiation used to excite the donor. In assays where the acceptor is luminescent, this means that there is usually a background of luminescence from the acceptor, even in the absence of any energy transfer from the donor and this in turn limits dynamic range of any assay using the donor-acceptor pair.

Exciting radiation is capable of exciting luminescence from impurities or other unwanted components of the sample.

The donor might emit some radiation at a wavelength which overlaps with the passband of the optical filters used to isolate emission from the acceptor, so that a signal is detected in absence of energy transfer.

These and related problems limit the scope, sensitivity and dynamic range of assays based on energy transfer processes.

BRIEF SUMMARY OF THE INVENTION

A method of detecting or quantifying an analyte by means of luminescence assay according to one embodiment of the present invention is based on detection of the transfer of energy between an energy donor species and an energy acceptor species as an acceptor of the energy in which the energy donor species is an up-conversion medium that affects a transition to an excited state by absorption of electromagnetic radiation having an energy less than that of the transition and is provided as a solid phase having a surface or is immobilized in a solid phase having a surface or is immobilized on a surface of a solid phase, and the acceptor species is bound to the surface of the solid phase in proximity to the energy donor species, the acceptor species when so bound being excited by energy transfer from the excited state of the donor species The specific method steps for this embodiment of the present invention include the steps of combining a sample potentially containing the analyte with the energy donor species and the acceptor species or a precursor thereof that is converted by the analyte to the acceptor species, irradiating the donor species with electromagnetic radiation to excite the donor species to its excited state for the energy transfer between the excited donor species and the acceptor species bound to the surface, and detecting luminescence in at least one spectral region of the emission of the donor species or of the acceptor if the acceptor is luminescent, provided that the excitation of the luminescent acceptor to a luminescent state emitting in the spectral region of the emission of the acceptor does not occur by absorption of a single quantum of the radiation used to excite the donor species.

It is therefore an object of the present invention to obviate or mitigate the abovementioned disadvantages.

DETAILED DESCRIPTION OF THE INVENTION

According to the present invention there is provided a method of performing an energy transfer luminescence assay to determine an analyte in which a donor species is irradiated to raise the donor species to an excited state, and the analyte causes a change in the excitation condition of at least one of the donor species and an acceptor species and said change is monitored to determine the analyte wherein
(i) the donor species is provided as, in or adsorbed to a solid phase and is an up-conversion medium capable of effecting, by energy pooling or otherwise, an energy transition to an excited state by absorption of electromagnetic radiation having an energy less than that of said transition,
(ii) the acceptor species is bound or is capable of being bound directly or indirectly to the surface of said solid phase,
(iii) the donor species is irradiated with said electromagnetic radiation, and
(iv) luminescence is detected in at least one spectral region characteristic of the emission of the donor species and/or the acceptor species provided that the excitation of the acceptor species to an excited state capable of luminescence in a defined spectral region of the acceptor species does not occur by absorption of a single quantum of the radiation used to excite the donor species.

The invention is based, therefore, on the use as the donor species of an upconversion medium which is capable of undergoing (by energy pooling or otherwise) an energy transition to the excitation state required for use in the assay as a result of excitation by photons which are of lesser energy than said transition. A further feature of the invention is that if an excitation condition of the acceptor species is monitored then such monitoring is in a spectral region which is a characteristic of the acceptor species and in which the latter has not been excited to a luminescent state by absorption of a single quantum of the radiation used to excite the donor. This ensures that, in the defined spectral region of the acceptor, any change in the excitation condition is due to energy transfer from the donor species and not due to direct excitation of the acceptor species by the electromagnetic radiation. This is easy to achieve given the relatively low energy of the electromagnetic radiation which may be used to excite the donor species. These features provide the advantage that the relatively low energy of the excitation photons minimises, and possibly eliminates, background problems and does not give rise to excitation of the acceptor in the absence of energy transfer from the donor species to acceptor species bound thereto.

A solid species has several advantages as an energy transfer donor. The solid matrix prevents or minimises collisional quenching of the donor emission by dissolved species such as ions or oxygen, and limits access of the luminescent species to water. Water can be an efficient quencher of many long-lived luminescent species, at least in part on account of its relatively high phonon energy which facilitates radiationless deactivation.

The solid matrix provides a relatively rigid environment conducive to long emission lifetime and high luminescence efficiency. Long lived excited states are appropriate to the present invention in that they are efficient as energy transfer donors by virtue of diffusional enhancement of transfer to species notionally bound at distances where otherwise energy transfer would be negligible, and are well suited to lifetime resolved detection methods which minimise background. In addition, the long lifetime of metastable intermediate states is important in multiphoton excitation schemes.

The solid matrix also provides a potential means to enhance sensitivity by allowing energy migration between luminescent species in the matrix. This allows distant excited species to contribute to energy transfer to a surface bound acceptor by first transferring energy to intermediate species until the energy reaches a site sufficiently close to the acceptor for efficient transfer to occur.

A further advantage of a solid medium is evident in that it provides a surface to which a wide variety of other species can be bound by standard protocols. This facilitates attachment of recognition ligands and similar molecules related to the analytical application. For example, antibodies, lectins, oligonucleotides, nucleic acids, biotin, proteins such as avidin or streptavidin or other materials able to bind selectively to a complementary substance might be required in a given analytical protocol.

The up-conversion medium may be one which undergoes the transition to its exited state by simultaneous or sequential absorption of two or more photons of the same or different energy, each of said photons being of lower energy than the transition and not being able to excite the acceptor species. The up-conversion medium may be one requiring a priming dose of energy to excite species therein to metastable levels which are required for the up-conversion process to be possible. For example, the up-conversion medium may be an electron trapping phosphor.

The up-conversion medium may be one relying on excitation of an organic molecule to an excited state which subsequently relaxes to a metastable level (e.g. a triplet state of the organic molecule) of longer lifetime than the original state. Subsequent absorption of a second photon may promote re-excitation of the metastable state to the excited state of the donor species which is capable of luminescence or transfer of energy to the acceptor. Alternatively, intersystem crossing from the metastable level may give rise to an excited state of different spin multiplicity that is itself capable of luminescence or transfer of energy to an acceptor.

The up-conversion process may be based on the excitation of lanthanide ions in an appropriate matrix.

The up-conversion medium may be such that exciting radiation is absorbed by one or more species and subsequently transferred to one or more other species which acts as the donor. In this case, the primary absorbing species may, for example, be the ytterbium ion and the donor species may be erbium or thulium ions.

The donor species which is excited by the up-conversion process may be one which is able to delocalise its excitation by internal transfer of energy between similar sites within the up-conversion medium. This delocalisation of excitation may result in transfer of energy from sites within the bulk of the medium to sites at or near the surface of the medium which are subsequently able to transfer energy to the acceptor species.

For use in the assay of the invention the solid phase which is or which incorporates the donor species is preferably in the form of a particle, most preferably one having a size of 10-100 nm.

The acceptor species may be one which is capable of luminescence on energy transfer from the donor.

As conventional in energy transfer assays, the transfer can only occur when the donor and acceptor species are in sufficiently close proximity as provided for by the binding of the acceptor to the donor.

In a first preferred embodiment of the invention, the assay may be one in which the analyte causes a change in the extent of binding between the solid phase of the donor species and the acceptor species. The assay may be conducted in a format in which the analyte causes an increase in the degree of binding of the acceptor to the donor. In this case, the change which is monitored in either the acceptor species or donor species is as a result of energy transfer from the donor to the acceptor. One example of such an assay format is one involving analyte mediated binding of the acceptor to the donor. Thus, for example, the surface of the phosphor may be provided with analyte recognition molecules (e.g. antibodies, oligonucleotides or lectins) and the acceptor may be linked to a species (e.g. a further antibody) capable of binding to the combination of the analyte and the analyte recognition molecule on the donor.

Alternatively the action of an enzyme or other catalytic species may be monitored by activation of coupling between donor and acceptor, either by catalysing formation of a linkage between them or by unmasking of protected groups on either or both of the donor and acceptor species, resulting in formation of a complex between the said species or formation of a chemical bond between them.

Alternatively the assay may be conducted in a format in which the analyte causes a decrease in binding of the acceptor to the donor. In this case, the change which is monitored in either the acceptor species or donor species is representative of a decrease in energy transfer from the donor. Thus, for example, for use in the assay the acceptor may be displaceably bound to the donor and the analyte is capable of displacing the acceptor thus providing a decrease in binding.

An example of such an assay would be the use of an enzyme to catalyse the cleavage of a linkage between donor and acceptor, resulting in a decrease of binding between them.

In a second preferred embodiment of the invention, the analyte may be one which affects the acceptance properties (for energy transfer from the donor species) of a moiety which is bound to the solid phase of the donor species, and/or which affects the ability of the bound moiety to emit luminescence consequent on excitation by said energy transfer.

For example, in accordance with this second embodiment:
(a) The assay may be used to monitor the formation or cleavage of a bond linking a quenching species or an enhancer of emission to the solid phase; or to a luminescent moiety bound thereto:
(b) The moiety may be one which is converted by the analyte to a luminescent species capable of accepting energy from the excited donor species. The moiety may, for example, be a pro-fluorophore:
(c) The moiety may be one which is a pre-existing luminescent label (excited by energy transfer from the donor species) whereof luminescence is quenched by the action of the analyte:
(d) The moiety may be one which is able to change colour as a consequence of the action of the analyte. In this case, the excited up-conversion medium is able to luminescence with an efficiency determined by the colour of the bound agent.

In all cases, energy transfer from the donor species to the acceptor may be determined by measurement of quenching of donor emission (or a related parameter such as change in donor decay rate) or by sensitised emission from the acceptor if this is also luminescent.

The donor species is preferably an infra-red up-conversion phosphor. Such phosphors are commonly inorganic crystals or glasses designed to absorb infra-red radiation and to give rise to visible luminescence and are commonly used for detection of emission from infra-red laser sources. In the present invention however, some or all of the excitation energy from the phosphor is transferred radiationlessly to the acceptor species and such transfer can be detected either as a quenching of the visible luminescence of the phosphor, or by luminescence from the acceptor species if the said species is capable of such emission.

A variety of up-conversion phosphors are known and fall broadly into two categories. One type is based on use of an electron-trapping phosphor where the phosphor is "charged" by exposure to visible or ultraviolet light or other suitable radiation and where infrared light empties the traps giving rise to emission as a result of recombination processes. Such phosphors are usually chemically unstable in aqueous media and typically require encapsulation in a polymer. In addition, they exhibit a time-dependent background glow after charging and thus are not ideal for present purposes. This type of phosphor will not be considered further, though it could in principle be used in an appropriately designed assay, especially if pulsed excitation and gated detection were combined to minimise the effects of the background glow. This is possible because the background emission of the electron-trapping phosphor typically has a very long decay time extending to many hours in some cases, while the luminescence emitted in response to long wavelength excitation is much shorter lived and can be easily discriminated from background on this basis.

A more suitable candidate is the energy-pooling phosphor where an emitting species is excited by sequential absorption of quanta of energy, either directly or more usually via a sensitising agent. Such phosphors have recently been proposed for solid-state three-dimensional displays activated by multiphoton absorbence (see "A Three-Color, Solid-State, Three-Dimensional Display" by E. Downing, L. Hesselink, J. Ralston and R. Macfarlane, Science, Volume 273, 30th August 1996, pages 1185-1189). Efficient systems are typically based on heavy metal fluoride-containing glasses of a variety of compositions designed to give low lattice phonon energy and hence allow efficient emission from ions in the matrix. The cited article discusses efficient phosphors giving rise to red emission (based on trivalent praesodymium ion as dopant), blue emission (based on trivalent thulium ion as dopant) and green emission (based on trivalent erbium ion as dopant), and discusses energy level diagrams for the upconversion processes in these materials. As sensitising agent, trivalent ytterbium ions are often used. A ytterbium-sensitised, erbium-doped system giving rise to green light on excitation at 900-1000 nm via a two-photon process and a ytterbium-sensitised, thulium doped system giving blue emission via a three-photon process have been known for many years. Other ions such as neodymium have also been used as sensitisers, particularly in the context of fibre-optic upconversion media for laser applications. In phosphors such as these, a sensitising agent transfers energy to a metastable state of the emitter which can, after suitable relaxation, accept further quanta leading to a higher excited state which emits at shorter wavelength than the exciting light. The phosphors themselves are typically stable glasses which can be fabricated as sub-microscopic particles by standard methods, or can be surfaces where the emitting species is implanted by diffusion or bombardment. For use in some types of assay it is convenient to be able to derivitise or otherwise modify the surface of the up-conversion medium to permit recognition agents such as antibodies and lectins to be attached. There are many standard methods to achieve this, ranging from simple physical adsorption of polymers, proteins etc. onto the surface to covalent attachment via linking groups such as organosilanes which bind to surfaces bearing hydroxyl groups. The glassy matrices typical of inorganic up-conversion phosphors are quite suitable for such modification.

Some inorganic glasses which are otherwise suitable as efficient upconversion media might not be stable in water or might suffer quenching at the surface when present as very small particles for assay purposes. In such cases, a protective molecular layer of a chemically—or physically adsorbed material would be advantageous to prevent or minimise access to water. Organosilanes with hydrophobic chains bearing terminal reactive groups for example can combine the role of surface protection from water and activation for ligand coupling.

A further possible implementation of the invention uses organic or inorganic polymers as the host for the up-conversion process. In this case it is important to ensure that the polymer is not able to deactivate the excited species too rapidly for the up-conversion process to operate. Typically, polymers with low phonon energy states are most suitable in this context.

It is also possible to use organic dyes in an up-conversion process. Twophoton processes and three-photon processes are well known in this context, but usually require a very high power density for useful efficiency on account of the low cross section for simultaneous multiphoton absorption. Examples where photons are absorbed sequentially are also well known and these can be efficient at much lower power densities than are required for coherent multiphoton processes. Anti-Stokes fluorescence as a result of either triplet recombination or triplet re-excitation to excited singlet has been known for many years and these processes are well understood. Triplet re-excitation to the excited singlet through intersystem crossing from vibrationally-excited levels gives rise to temperature-dependent delayed fluorescence and has been used in optical thermometry (J. C. Fister et al, Anal. Chem. 1995 67 4269-4275). This publication points out that the rate of intersystem crossing is much slower than the rate of thermal equilibration between vibrationally-excited levels, so that the vibrational levels are populated according to the Boltzmann distribution. Any attempt to populate the excited singlet by excitation of vibrational levels of the triplet through photon absorption is likely to be inefficient on this basis, because the excess vibrational excitation will be lost within picoseconds. However, in some circumstances the excited singlet can be populated through intersystem crossing from a higher energy triplet state excited by means of the allowed triplet-triplet transition and this can be an efficient process in principle.

Organic dyes can be used both in inorganic matrices such as sol-gel glasses and in organic polymer matrices. Immobilisation of dyes in such matrices usually increases the lifetime of triplet states markedly and this increases the probability of further absorption to excite the triplet back to the excited single manifold. Although immobilisation might be expected to decrease the probability of up-conversion processes based on triplet-triplet annihilation, this need not be so because dyes can form clusters in the matrices and annihilation processes can be highly efficient in these circumstances. In some cases the polymeric matrix or a co-dissolved dopant can act as an energy donor to the luminescent organic material and excitation energy can be delocalised, for example by exciton migration within the matrix. Such systems allow energy to be transferred to sites which are remote from the point of primary absorption.

In an advantageous embodiment of the invention, the solid phase which is or which incorporates the upconversion medium is provided with a continuous, discontinuous or partial coating of a metal for the purpose of enhancing transfer of energy from the upconversion medium to the acceptor species. Thus energy from the upconversion medium can excite the metal layer which is capable of transferring energy to the acceptor.

For this embodiment, the solid phase may (for example) be in the form of a film or in the form of particles. The metal coating on the solid phase may be continuous, discontinuous or partial .

Analyte recognition molecules (see supra) maybe immobilised on the solid phase or the metal and be capable of directly or indirectly binding the acceptor species in close proximity to the metal surface, preferably within 10 to 200 nm, more preferably 10 to 50 nm, thereof (see also below). If continuous, the metal coating may be in the form of a film and the analyte recognition molecules may be bound thereto. If discontinuous then the metal layer may be formed from metal particles or clusters of colloidal metal and the analyte recognition molecule may be bound either to the metal or (more preferably) to the solid phase at discontinuities in the metal coating.

Apart from the presence of the metal coating, assays employing the metal coated solid phase may be performed in the same manner as described above.

The excitation of a metal for transferring energy from the metal to another species is known. For example an excited metal film can itself act as an energy donor to an acceptor molecule bound to the film, the acceptor molecule then being detectable by fluorescence or by Raman scattering. The amplification of fluorescence of surface-bound fluorophores by metal films is well known. Fluorescently-labeled protein molecules have been detected on binding to a variety of thin metal films using surface-plasmon mediated enhancement of excitation, for example ('Single molecule imaging of fluorescently labelled proteins on metal surfaces by surface plasmons in aqueous solution', Hiroaki Yokata, Kiwamu Saito and Toshio Yanagida, Physical Review Letters, 1998 vol. 80, no. 20, pp. 4606-4609). Fluorescence excitation is said to be most markedly enhanced on interaction of labels with 'fractal' aggregates of metal particles, particularly if these are placed in optical cavities ('Fractals in microcavities: giant multiplicative enhancement of optical responses', Kim, W., Safonov, V. P., Shalaev, V. M. and Armstrong, R. L., Physical Review Letters, 1999, vol. 82, no. 24, pp. 4811-4814).

The use of metal particles or coatings to enhance excitation of fluorescence arid to enhance Raman scattering in surface binding assays has been disclosed in U.S. Pat. No. 5,837,552 ('Surface-enhanced analytical processes and substrates', T, M. Cotton et al 1998) and related patents. This patent discloses a sensor surface comprising spaced islands of metal with at least some interconnections, on which a continuous layer of a binding agent is deposited. In addition, the use of fractal metal particles in microcavities has been disclosed in WO-A-0115288 ('Optical enhancement with nanoparticles and microcavities', Armstrong, R. L., Shalaev, V. M., Shay, T. M., Kim, W- T. and Ying, C.) and related patents. In U.S. Pat. No. 5,866,433 ('Optochemical fluorescence sensor and method for measuring the concentration of at least one analyte in a sample', Schalkhammer, T., Pittner, F., Leitner, A., Aussenegg, F. and Brtinner, H. (1999)) a method to detect analytes based on enhancement of fluorescence by metal island of diameter <300 nm is described, where the sample is bound either directly to the surface of the metal or via a spacer to minimise fluorescence quenching by the metal. In U.S. Pat. No. 5,449,918 ('Amplified fluorescence emission for chemical transduction', Krull, U. J. and DeBono, R. F. (1995)) surface plasmon resonance in metal island films is used to enhance fluorescence from bound species.

In the prior art cited, a sensor surface is illuminated with a source of light in order to excite surface states such as plasmons, and the wavelength of this incident illumination is the same as would normally be used to excite the fluorescence from a fluorescent species bound to the metal. The metal surface absorbs the light and merely acts as an amplifier, enhancing the local electromagnetic field. In such applications, the radiation used to excite the surface bound species via the intermediacy of the metal coating will also be able to excite any similar unbound labels. Thus, if a sample having a substantial concentration of free fluorescent label in addition to surfacebound species is so illuminated, fluorescence will be excited from the solution species as well as the bound species.

In contrast, in the present invention, metal films or particles adsorbed to upconverting surfaces are illuminated with long wavelength (typically infrared) light that cannot efficiently excite the acceptor (e.g. a fluorescent species) directly whether the acceptor is free in solution or bound to the surface. The metal associated with the surface of the solid phase is excited by accepting upconverted energy from the donor and little of this escapes from the coating to excite species in solution. As a consequence, only surface-associated acceptors are excited efficiently as a result of the upconversion-mediated excitation of the metal surface.

The use of a metal coating to act as a "primary acceptor" of energy from an upconverting surface, and thereafter to transfer energy on to an absorbed species (so that the metal acts as a "relay"), is a particularly attractive method to detect surface binding of fluorescent or phosphorescent labels as the acceptor species in the method of the invention. A metal coating (which might or might not be continuous, and could for example be an adsorbed colloid or a deposited film) can act as a very effective means to localise the energy of upconverted luminescence into a spatial region that is able to transfer energy to a bound acceptor species. In absence of such a coating, the transfer of excitation energy by resonance energy transfer from an upconverting surface to a bound absorbing dye or fluorophore, for example, is limited to species within a few nanometres from the surface. Thus, if a relatively large upconverting particle is used, much of the upconversion species within the particle will be unable to transfer energy efficiently to a bound acceptor. However transfer of energy to a metal at the surface of the upconversion medium is not mediated solely by resonance energy transfer. Radiative processes can contribute to excite the metal, which can absorb some of the emitted radiation directly as a consequence of the relatively high optical density that can be achieved using a surface-associated metal film or aggregate. This means that energy can be accepted from distant sites within the upconverting material, so that relatively large particles or thick films of upconverting materials can be used. This is a major advantage, because upconversion efficiency is much higher for large particles or thick films than for most nanoscale structures.

Once the metal is excited, the onward transfer of energy to bound acceptors such as fluorophores has a distance dependence that is less steep than that of resonance energy transfer. Excitation energy is transferred through the evanescent component of the electromagnetic field at the surface of the metal, and this can penetrate beyond the surface and decays exponentially in space through distances of hundreds of nanometres. This allows detection of surface bound fluorescent or phosphorescent macromolecules, where the molecular size might be too great to allow efficient resonance energy transfer directly from an excited fluorophore.

Metal-enhanced photoluminescence has several distinctive features that can be useful in the present context. It is well known that proximity to metal can alter the effective quantum yield of a fluorophore, and that relatively weakly fluorescent samples can sometimes be detected much more efficiently by this means. It is also possible in principle to enhance excitation of weakly allowed transitions by metal-induced perturbations. These aspects extend the scope of the present invention.

A further attractive feature of the use of metal-coated surfaces for upconversion assays is that the metal itself can serve a dual role in principle. Excitation of the metal by infra-red radiation can be used to transfer energy to the upconversion medium with good efficiency. In this case the metal acts as an energy donor with the transfer to the upconversion species being mediated by surface plasmons/polaritons excited by infrared light. Visible or UV luminescence from the upconversion can then couple back to the metal to excite appropriate plasmon/polariton oscillations that can transfer energy to bound dyes or fluorophores, for example.

Although a number of metals have been used in the prior art for enhancement of photoluminescence from surfaces, silver and gold are most commonly employed. Both silver and gold show marked enhancement effects and they are able to link to biological materials through chemical binding of thiol groups for example. Thus gold and silver are preferred metals for use in the invention.

It is well known that electronically excited species that are within a few nanometres of a metal film can lose their energy by resonance transfer to the metal, and hence any fluorescence or phosphorescence from these species can be 'quenched'. In the prior art,this problem is often avoided by providing a metal surface with a nanometre-scale coating of an inert material to act as a spacer and this technique can also be used in the present invention. The optimum thickness of this coating depends on the effective transfer radius for the resonance process, which depends in turn on the spectral overlap between the emission spectrum of the luminescent species and the absorption spectrum of the metal. However the distance dependence is a steep function so that the effective distance at which 50% of the excited species are deactivated by transfer of energy to the metal surface (the so-called 'Ro' value) is similar for most fluorophore/metal combinations, and typically is of the order of 3-7 nm. Doubling this distance reduces the energy transfer efficiency by a factor of 64, as the process scales with a sixth power dependence. Thus a coating of the order of 10 nm suffices to reduce metal quenching of fluorescence to a low level. Luminescence is enhanced at metal surfaces through plasmon-mediated processes that are still effective for species bound to the spacer, whereas the quenching processes are suppressed because the distance between the label and the metal is too great for efficient energy transfer. The evanescent wave component responsible for metal-induced enhancement of luminescence decays exponentially in space with a decay length that depends on the wavelength of the exciting radiation and the refractive index of the rarer medium. Typically the evanescent wave can excite fluorescence at distances greater than 50 nm, so that efficient excitation is possible without significant associated metal-mediated quenching. For the purposes of the present invention therefore, preferably the fluorescent species are bound at a greater distance that that associated with the 'Ro' value for the metal and fluorophore of interest, and most preferably at least twice this distance. Given that the efficiency of metal-mediated enhancement of fluorescence decays exponentially, there is no advantage in positioning the fluorophore at a greater distance than this, but if necessary useful enhancement can be achieved at substantially greater distances, typically up to distances of the order of 200 nm. Preferably therefore the luminescent species is bound at a distance of between 10 and 200 nm of the metal surface, more preferably between 10 nm and 50 nm.

An alternative approach where metal islands are used is to ensure that fluorescent species bind in between the islands rather than directly onto them. This can be achieved by coating the surface first with a binding layer to allow labels to become attached at a later stage, and coating this binding layer with a metal to form islands. In this way the metal blocks off binding sites where it is deposited but leaves the surface free to bind labels in the intervening spaces. This method is to be distinguished from that described in prior art such as U.S. Pat. No. 5,837,552, where a continuous film of a binding agent is used that covers both the islands and intervening spaces. The metal coating can be applied in a number of ways such as sputtering, evaporation, chemical or photochemical deposition or adsorption of preformed colloids. The distance scales that apply to the metal-mediated quenching and enhancement processes for species bound between such discontinuous coatings are the same as was previously described for spacer layers on metal films.

The upconverting agent with associated metal coating and analyte recognition agent can be used as a suspension in an aqueous medium or else can be used as a film or coating on a surface, for example in the well of a microtitre plate.

In accordance with a further aspect of the invention there is provided a microarray analytical device comprising a plurality of spatially distinct microscopic regions each comprised of binding ligands wherein said ligands are provided on or in close proximity to the surface of an associated metal coating, said device further comprising donor species provided as, in or adsorbed to a solid phase and being an upconversion medium capable of effecting an energy transition to an excited state by absorption of electromagnetic radiation having an energy less than that of said excited state, said metal coating being provided on the donor species.

In the microarray, the solid phase (which is or which incorporates the donor) may be a continuous layer. In this case, the metal coating may also be continuous and the binding agents are provided as discrete islands on the metal coating. Alternatively, discrete metal islands may be provided on the continuous metal phase with each metal island being associated with appropriate binding agents.

It is also possible for the solid phase (which is or which incorporates the donor) to be provided as islands, each associated with a metal coating and appropriate binding agents.

Thus, microarrays can be constructed where either an upconverting surface has a periodic array of metal structures associated therewith, or where the surface of a substrate such as a glass slide has metal-coated upconverting material deposited as a film or an array of discrete regions associated with appropriate binding agents. A fluorescence microscope modified to allow excitation in the far-red/near infra-red spectral region provides an efficient method to measure the sensitised photoluminescence from such microarrays.

Where an extended film of upconverting material is used it can be convenient to provide the metal coating as a spatially-periodic structure such as a grating. It is well known that such gratings provide an efficient method to couple energy into surface states of metal films in appropriate circumstances.

A further aspect of the invention provides a method of determining an analyte by means of a luminescence assay comprising the steps of (i) incubating a microarray as defined above with a sample including an acceptor species that is bound or is capable of being bound directly or indirectly to the surface of said solid phase and is capable of being excited by energy transfer from the donor species, (ii) irradiating the donor species with electromagnetic radiation, to excite the donor species to the excited state, and (iii) detecting luminescence in at least one spectral region characteristic of the emission of the donor species and/or the acceptor species provided that the excitation of the acceptor species to an excited state capable of luminescence in a defined spectral region of the acceptor species does not occur by absorption of a single quantum of the radiation used to excite the donor species characterised in that the analyte causes a change in the excitation condition of at least one of the donor species and an acceptor species as a result of the acceptor species being bound to or released from the solid phase and said change in monitored to determine the analyte.

The invention further provides apparatus comprising
(i) a microarray as defined above
(ii) a continuous or pulsed source of excitation of a wavelength that can excite upconverted radiation from the microarray,
(iii) means to direct the said excitation to the surface of the microarray,
(iv) optical means to isolate emission in a wavelength range characteristic of the photoluminescence of said bound species while rejecting substantially all of the exciting radiation and of the upconverted emission from the microarray, and
(v) means to detect the characteristic photoluminescence emission of the bound species.

The microarray can be excited by means of a focused light source equipped with a filter to isolate the (typically near infra-red) emission used to stimulate upconversion. In this case the microarray will be positioned so that a given spatial region of interest is at the focus of the exciting radiation, and emitted radiation will be collected by an objective lens, passed through an interference filter to isolate the spectral region of interest and detected with a conventional detector such as a photomultiplier or semiconductor detector.

An alternative approach is to excite the microarray by coupling light into it using a prism or grating so that the microarray acts as a waveguide and the excitation is totally-internally reflected within. In this configuration, it is convenient to collect emission from several spatially distinct binding regions simultaneously using a lens to image the surface of the microarray, in conjunction with a sensitive camera such as a CCD detector equipped with an interference filter to block unwanted signals not associated with the photoluminescence of the bound species.

In the method of the invention, detection of the excitation condition of the donor species and/or acceptor species may, for example, be effected by a semiconductor diode, a linear charge-coupled device (CCD), MOS sensor or an imaging detector. Such an imaging detector may utilise an image intensifier or imaging single photon detector. Alternatively the imaging detector may be a CCD camera or other solid state imaging device.

It is well known that multiphoton excitation can be achieved using a continuous light source of sufficient intensity ("*Two-photon excitation fluorescence microscopy using a semiconductor laser*", P. E. Hanninen et al, Bioimaging, (1995), 3(2), 70-75), and that such excitation can be achieved without unacceptable damage to a specimen. According to the above publication, a principal limitation on the optical power which could be applied to a sample was set not by photochemical damage, but by the "optical tweezer" effect where intense beams of radiation exert forces on microscopic objects.

The main difficulty in the use of a continuous excitation source is the requirement to reject background signals, since radiation is present at all times during the measurement. This background rejection need not be a problem if the detector used does not respond at the exciting wavelength(s). Where this is impractical the exciting radiation often can be rejected very efficiently by optical filters. For example, as described in "*Time-Resolved Fluorescence Microscopy using Two-Photon Excitation*", P. T. C. So et al, Bioimaging, (1995), 3(2), 49-63 a simple filter based on a solution of copper sulphate achieved an effective optical density of 20 for an exciting long wavelength radiation (i.e. the ratio of incident to transmitted light was $10^{20}$) while transmitting approximately 70% of a two-photon-excited fluorescence which was to be detected. Nevertheless, such efficient optical rejection cannot always be realised, and other methods to reject scattered light are sometimes required. One such means to achieve selective detection of upconverted luminescence is to exploit the non-linearity of the excitation process.

This leads to a further aspect of the present invention according to which there is provided a method of detection of luminescence in which a luminescent species of interest is excited by a process of simultaneous or sequential absorption of at least two photons from at least one photon source, wherein the or each photon source is modulated at one or more frequencies, and luminescence measurements are made at a frequency or frequencies different from the or each modulation frequency, the or each frequency at which measurements are made being a function of the or each modulation frequency by virtue of the excitation process.

A single excitation source may be provided, the source being modulated in for example intensity at a frequency F. Any background of scattered light originating from the source will be modulated at the same frequency. Any luminescence excited by a single photon process will also be modulated at F, with a relative modulation depth determined by the frequency of modulation in relation to the lifetime of the excited state of the single photon process. Although fluorescence excited by a long wavelength radiation is normally of lower energy than the excitation, shorter wavelength "Anti-Stokes" emission is possible and is sometimes seen where high intensity excitation is used. If however a two-photon excitation process is occurring, then resulting emissions will have a component fluctuating at 2 F (higher frequencies will occur for higher order multiphoton processes). Relative modulation depths of each component will depend on the lifetime of the excited states relative to the modulation frequency, and a suitable frequency may be chosen to give appreciable modulation of a desired excitation process. It is a simple matter to detect a signal fluctuating at 2 F in the presence of a constant background or signal fluctuating at F.

In principle the above single frequency technique is a powerful means to reject background frequencies through multiphoton excitation. However, a potential difficulty may be the presence of harmonic distortion in the modulated light source. If such distortion is present there may well be a component of excitation fluctuating at 2 F, 3 F or other multiples of the fundamental. Scattered light or ("Anti-Stokes") single-photon-excited fluorescence will then be detected at harmonics of the fundamental as if it were the desired multiphoton-excited emission. Most techniques used to modulate light give rise to some level of harmonic distortion, and the introduction of harmonic distortion will always be a potential problem.

In order to overcome such potential problems resulting from harmonic distortion, it is preferred to use a single source modulated with a composite waveform comprising the sum of two or more different frequencies, measurements being made at a frequency which is a linear combination of the different frequencies. Digital or analogue techniques may be used to achieve the desired modulation and in the former case the luminescence measurement may be recovered conveniently by Boolean logical analysis of a detected signal. The method of detection is particularly suited to an emitting species with a long luminescence decay time such that emissions excited by the source or sources are not able to reproduce the modulation frequencies but are able to reproduce frequencies corresponding to a difference frequency, measurement being made at the difference frequency.

This allows the presence of an interfering species capable of luminescence as the result of multiphoton excitation processes, but with a shorter luminescence lifetime than the species of interest, to be detected. Measurements are made at one or more frequencies selected such that a signal from the species with the long decay time will suffer substantial attenuation by virtue of demodulation while a signal from the interfering species will not suffer substantial attenuation.

Suitably, measurements are made at frequencies that are the sum and difference of the modulation frequencies, and a function of the result of the measurement at the sum frequency is subtracted from a function of the result of the measurement at the difference frequency to suppress contributions from short-lived emissions. In some cases it may be necessary or experimentally convenient to excite upconverted luminescence by illuminating the sample with two or more light sources of the same or different wavelength. For example, two excitation sources may be chosen so as to match the energies of individual electronic transitions involved in the upconversion process, or light sources of the same wavelength may be focused onto a common point. In such cases the individual sources can be modulated and measurements of luminescence made at one or more frequencies present by virtue of the non-linearity and/or multiplicative nature of the upconversion process.

The exciting radiation may be provided by a semiconductor light-emitting diode or laser. The exciting radiation may be pulsed or modulated in intensity in which case gated detection may be used to confine detecting signals to one or more defined time period relative to the excitation. The detection system may use a periodically switched, gated or modulated detector to implement lock-in detection or similar correlated detection schemes. For example, the detector may be an imaging detector which is gated or modulated in sensitivity. Alternatively an imaging detector may be designed to implement phase sensitive detection in conjunction with a periodic excitation source.

An up-conversion phosphor as described above is particularly preferred for use in the invention since it solves many of the background problems when used as a component in an energy transfer system.

The exciting radiation is not sufficiently energetic to excite background from the sample or surroundings at a wavelength which will interfere with the measurement.

Suitable sources of high intensity pulsed near infrared radiation are very low cost solid state devices.

Detectors such as photomultipliers are insensitive to the near infrared radiation, which can in any case be rejected very efficiently by low cost optical filters.

The visible emission from the phosphors is highly structured, facilitating spectral discrimination in the event of any overlap between donor emission and that of the acceptor.

The excited state lifetime of the phosphor is relatively long. Consequently the method lends itself naturally to lifetime-resolved detection. This mode of operation is insensitive to stray light, so that background from this source is greatly reduced.

When time gating is used with a pulsed light source a simple photodiode will give good detection efficiency, because the signal is concentrated in a short pulse and dark current can effectively be ignored. Although the diode might have some sensitivity to any residual infrared light leaking through optical filters, time gating will eliminate this.

In addition to the detection of luminescence using a photodiode or photomultiplier, the method lends itself to detection using an imaging detector or linear array. Suitable detectors include image intensifiers (which can additionally be gated or modulated in sensitivity), linear MOS sensors or CCDs and various types of semiconductor area detector such as CCD cameras. Some types of CCD camera can be gated, for example by control of the active imaging period by suitable manipulation of the charge drain facility in conjunction with the charge storage and transfer facilities of the camera. Alternatively, the camera can be equipped with an optical shutter capable of single or periodic operation. Suitable liquid crystal shutters are presently available and have been used previously for phosphorescence detection with a CCD camera.

Imaging detection of luminescence in the context of the present application is appropriate for example to simultaneous measurement of samples in multiwell plates, such as are widely used in immunoassays and similar analytical applications. In such applications it might be advantageous to illuminate the sample with an array of semiconductor light-emitting diodes to furnish the required long wavelength excitation, though of course other sources of photons such as pulsed flashlamps could also be used.

The excitation process is proportional to the square or higher power of the infrared exciting radiation. This means that in a focused beam, emission is mainly seen from the focal plane. This is potentially advantageous in an assay, because it avoids problems of signal originating from the container or from background outside the focal region. It is also possible to excite the sample simultaneously with two or more sources of photons of differing wavelength, in which case the efficiency of excitation will be proportional to the product of the individual photon power densities (or to the product of the square, cube or other exponents of each of the photon densities).

Some types of up-conversion media have a further advantage when used as the donor species and this is particularly (though not exclusively) so with those phosphors in which the up-conversion process involves lanthanide ions within a suitable matrix. within the up-conversion medium, energy is transferred by a near-resonant process between ions of the emitting species. This very efficient transfer means that the excitation is effectively delocalised. If an energy acceptor approaches closely enough to any ion for efficient energy transfer to be possible, it is also possible for energy from a more distant ion to migrate through the lattice and reach the acceptor which acts as an energy "sink". This means that a single acceptor can be excited by ions which otherwise would be too far away for energy transfer to be efficient. The process gives rise to an amplification mechanism, since a given acceptor can be excited many times from a given excitation pulse. In practical terms the effect is also advantageous, because otherwise only very small phosphor particles would be efficiently quenched by energy transfer to the acceptor. Similarly, in the case of an assay format involving detection of binding to an extended surface, such as for example the surface of an optical fibre doped with up-conversion medium, the effect allows energy to be accepted from a greater depth within the surface than would otherwise be the case.

Although the most commonly encountered mechanism of energy transfer between organic species is a dipole-dipole mechanism, other mechanisms are possible including multipole effects, electron exchange processes and surface effects involving plasmons. For this reason, suitable energy transfer acceptors are not limited to simple organic dyes or fluorophores but may be inorganic substances (e.g. colloidal inorganic semiconductors such as zinc selenide) which have an absorption spectrum overlapping the emission from the donor species or which can act as energy acceptors by other means such as electron exchange. Colloidal metals (e.g. colloidal gold and silver) are also potential acceptors for energy from the donor. Colloidal gold is commercially available derivatised with a variety of surface-bound ligands such as antibodies for applications in conventional assay procedures. Amplification processes such as the widely-used silver enhancement method for colloidal gold labelling might also be applied to increase the effectiveness of such labels as acceptor species by increasing the amount of bound colloid and inducing greater absorbence at the particle surface. If desired, the metal acceptor may have a luminescence species bound to its surface, the luminescence species being excited by energy transferred from the metal particle. In this case, it is possible to monitor emission of this luminescence species to follow progress of the analysis procedure.

Figure 1:
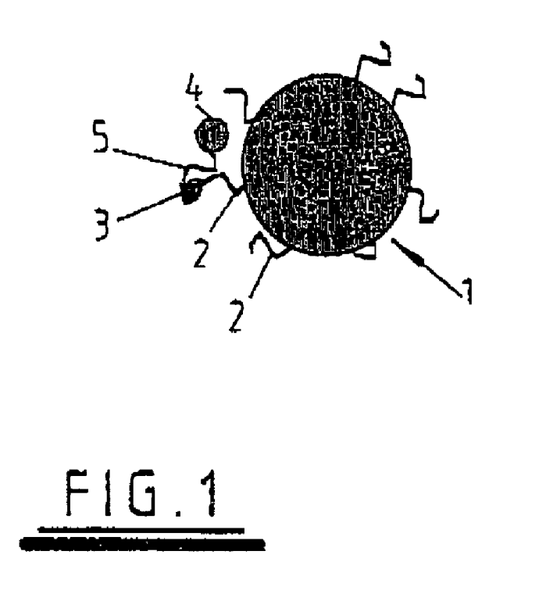
FIG. 1 schematically illustrates (not to scale) an up-conversion phosphor involved in analyte mediated binding of a fluorescent dye as acceptor species in accordance with the first preferred embodiment of the invention.

Referring to FIG. 1, there is illustrated a phosphor particle 1 having a size of 10 to 100 nm comprised of a mixture of Ytterbium and Erbium ions in a glassy matrix. Attached to the outer surface of particle 1 by covalent bonding or adsorption are antibodies 2 to which an analyte molecule 3 will bind. As further illustrated in FIG. 1, an acceptor species 4 (in the form of a dye molecule) is bonded to further antibodies 5 which are capable of binding to the complex formed between the analyte 3 and the antibodies 1 such that the acceptor species (now located within close proximity of the particle 1) is capable of having energy transferred thereto from an excited state of the phosphor.

Figure 2:
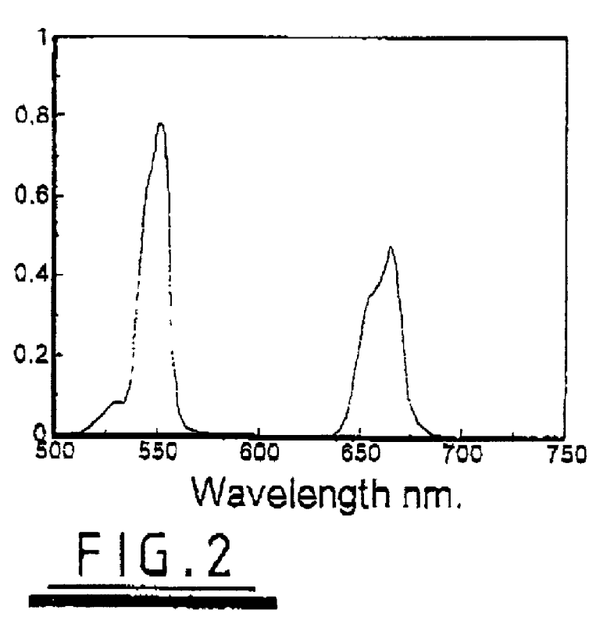
FIG. 2 illustrates the emission from a Ytterbium-sensitised Erbium-doped up-conversion phosphor.

The emission from a typical Ytterbium-sensitised Erbium-doped up-conversion phosphor excited at 980 nm is shown in FIG. 2 below. As is evident, there is a clear spectral region where luminescence from an energy acceptor could be measured without interference from phosphor emission. In the case of this phosphor dyes such as Rhodamine 6G, sulforhodamine 101 and Cresyl Violet would be suitable as energy acceptors with fluorescence in the region where the phosphor does not emit, though of course there are many other fluorophores which could be used.

Figure 3:
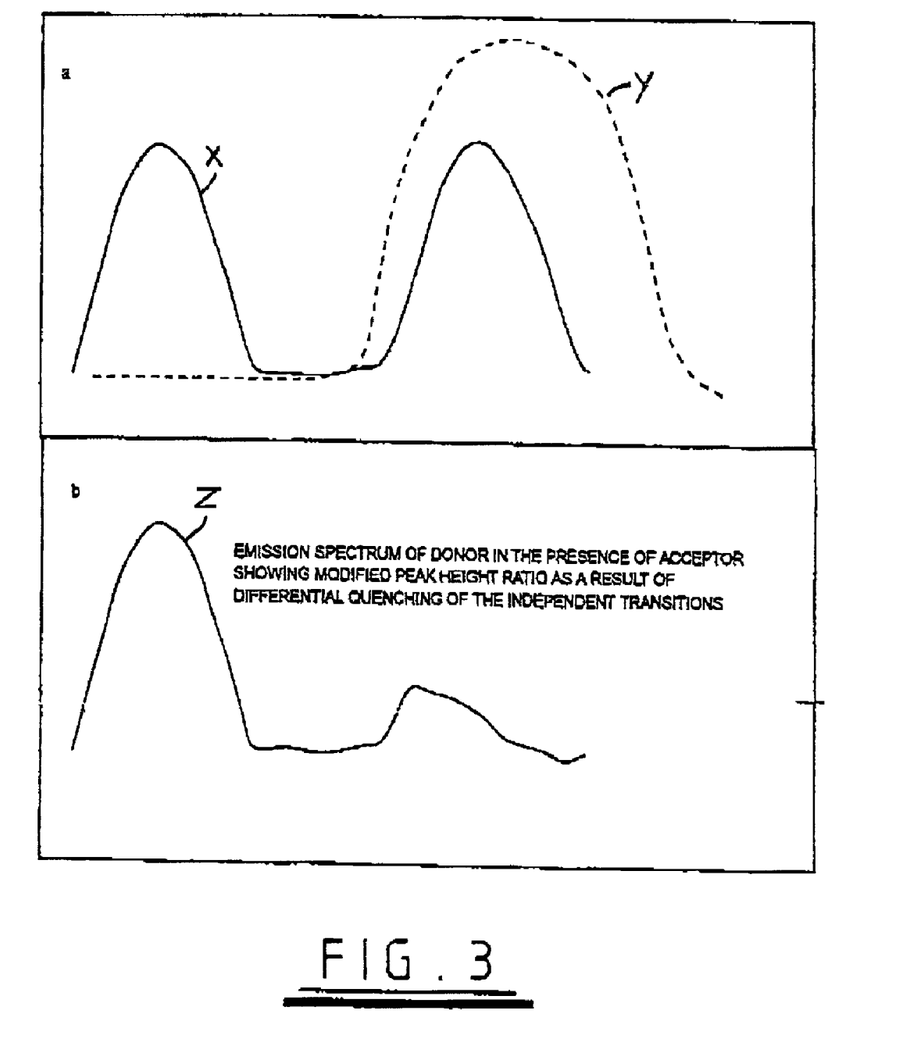
FIG. 3a-3b illustrates the situation where the donor species has independent emission transitions which are differently affected by energy transfer to an acceptor species.

In the example shown, there are two well separated emission peaks. In case where such transitions are independent it is likely that the emission peaks will be quenched to different extents by energy transfer to an acceptor, particularly where the absorption of the acceptor overlaps one emission peak more than the other. This is shown in FIG. 3 which illustrates the situation where the donor species has independent emission transitions which are differently effected by energy transfer to an acceptor species, e.g. a case where the acceptor absorbence is greater for one errission peak than for the other. In FIG. 3a, the peak X represents the emission spectrum of the donor species and the peak Y represents the absorption spectrum of the acceptor. FIG. 3b shows the emission spectrum Z of donor in the presence of acceptor showing modified peak height ratio as a result of differential quenching of the independent transitions. The ratio between emissions in the component peaks can be used to determine analyte binding, much as wavelength ratio measurements with fluorescent ion-sensitive dyes are used to quantify ion concentrations in biology. These measurements are advantageous when the energy acceptor acts simply to quench emission from the donor, and is not itself luminescent. Ratio measurements are independent of the amount of the donor species, but depend on the relative amounts of free and acceptor-bound species. Such ratio measurements can be conducted without time resolution, but are compatible with time-resolved measurements or equivalent frequency domain measurements for enhanced background rejection. Where the upconversion medium does not have appropriate independent transitions, it may be possible to introduce a suitable reference dopant (which need not necessarily be excited by multiphoton means, though would advantageously have long-lived luminescence).

Figure 4:
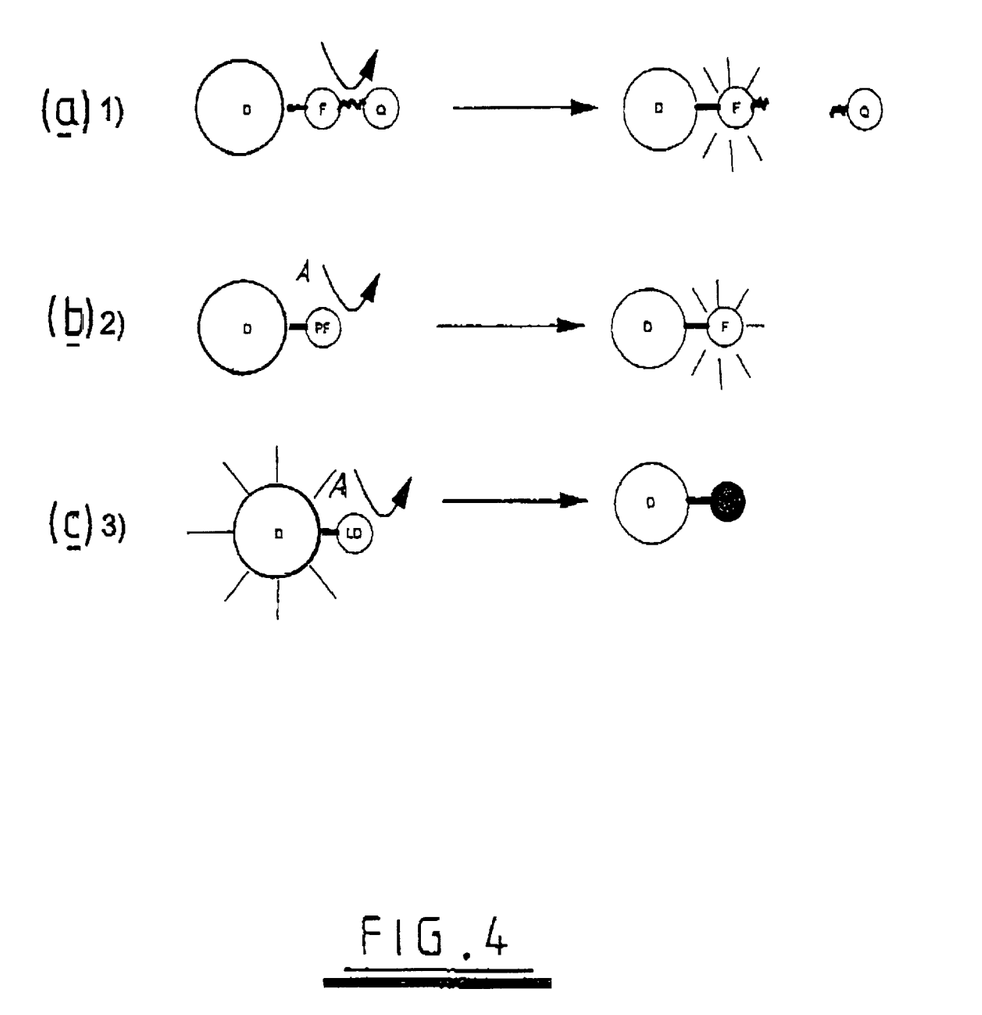
FIG. 4a-4c schematically illustrates assays in accordance with the second preferred embodiment of the invention.

Reference is now made to FIG. 4 which schematically illustrates assays in accordance with the second preferred embodiment of the invention.

FIG. 4a illustrates an assay in which the analyte A causes cleavage of a bond linking a quenching species Q to a bound luminescent (e.g. fluorescent) label F. When Q is cleaved from F by the action of the analyte the luminescent label F is able to fluoresce as a result of energy transfer from the excited donor. The excitation condition of D or F may be monitored to determine the analyte.

FIG. 4b illustrates an assay in which a pro-luminophore, e.g. a pro-fluorophore (PF) is converted to a luminescent species by the action of the analyte A. The pro-luminophore is attached to the surface of the up-conversion medium. The action of the analyte results in the generation of a luminescent substance able to accept energy from the excited up-conversion medium. In this case the emission of the luminescent product is sensitised by the up-conversion medium and has the same time course as the decay of the excited medium. Thus, for example, in the event that a short lived luminescent species is bound to the surface of an energy donor of long excited state lifetime, then the sensitised luminescence of the acceptor will also have a long decay time and can be detected by time gated methods or equivalent as discussed previously. Such lifetime-resolved detection has been used previously in luminescence assays using conventionally excited donors. The present invention has the advantage that background luminescence will not be excited efficiently by the excitation source used to activate the up-conversion medium.

FIG. 4c illustrates an assay in which a colourless species, e.g. a leuco-dye (LD) is bound to the solid phase of the up-conversion medium and is converted to a coloured species by the action of the analyte A with associated quenching of donor emission.

All of the assays shown in FIGS. 4a-c may be effected in "reverse". Therefore, for example, the assay of FIG. 4b may be operated in a manner such that the analyte converts a fluorescent species to a non-fluorescent species. In the case of FIG. 4c the assay may be effected such that the analyte converts a coloured species to a non-coloured (or differently coloured) species. A ligase or similar enzyme might catalyse bond formation rather than cleavage in the example of FIG. 4a.

Figure 5:
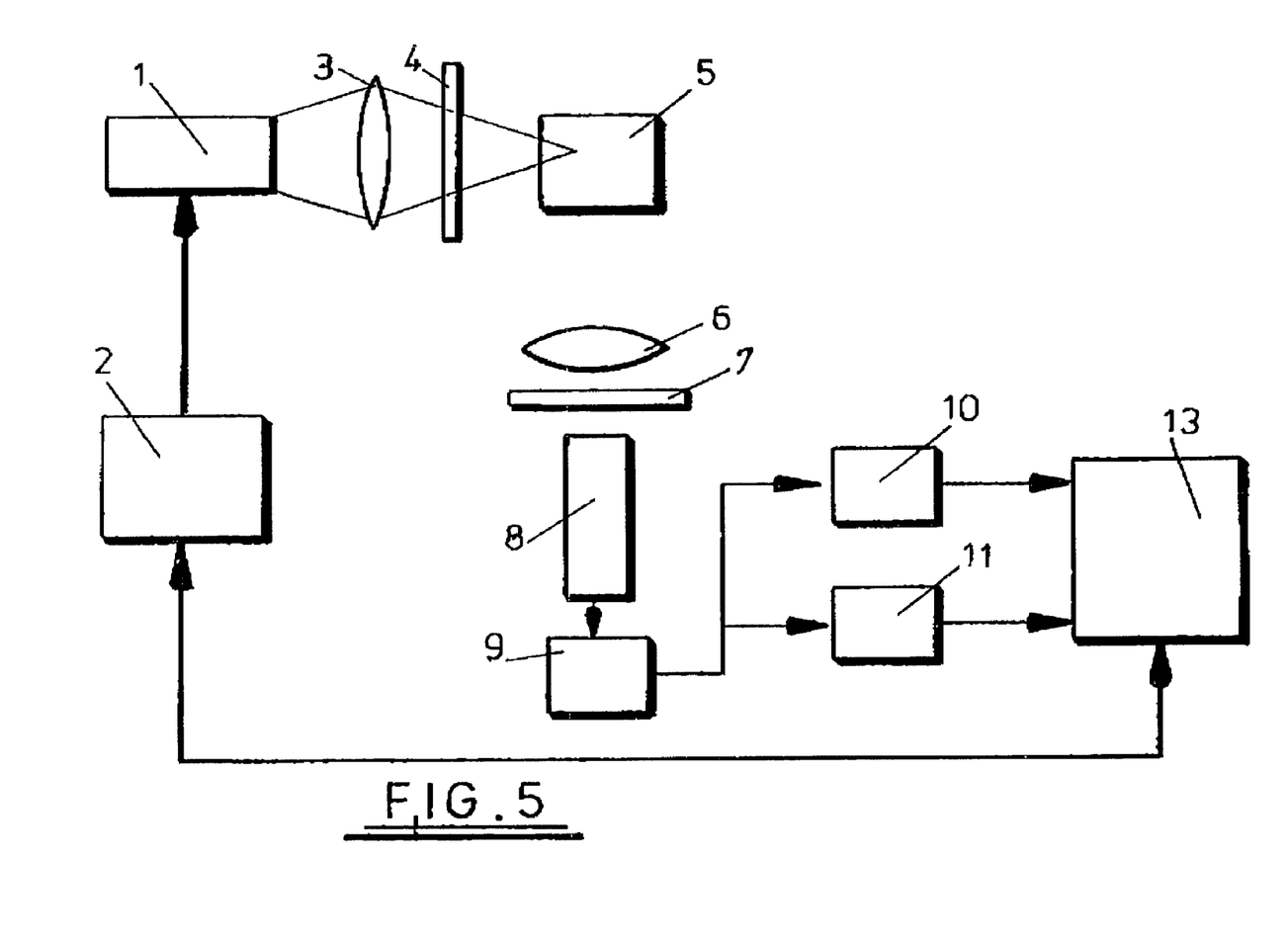
FIG. 5 is a schematic diagram representing a configuration of apparatus for detecting upconverted luminescence.

A configuration for the excitation of luminescence by a single light source 1 is shown in FIG. 5. A waveform generator 2 provides a modulation signal with at least two frequency components to the light source 1. Which is focused to a beam by a lens 3 and unwanted wavelengths are rejected by an optical filter 4. Focused light is incident on sample 5 and luminescence from the sample is collected by lens 6, optically filtered by filter 7 and detected by detector 8 which is an electronic device such as a photomultiplier or semiconductor detector. The detected signal is amplified and optionally filtered by a signal-conditioning unit 9 and is furnished to optional frequency selective elements 10 and 11. The outputs of these elements, or of unit 9 directly, are fed into a control system 13 which is a computational device able to analyse the frequency distribution of the signal(s) and optionally to control the operation of the electronic drive means (unit 2).

Although the description in relation to FIG. 5 is directed to the use of a single light source, it is to be understood that light source 7c could be replaced by individually controlled, multiple sources.

If the luminescence decay time of a species sample is long, it is particularly convenient to excite the sample with a source or sources whose individual modulation frequencies are sufficiently high that emission will be unable to reproduce fluctuations at the or each modulation frequency or at higher frequencies. In this case, a difference frequency can be chosen to be low, so that the only component of the detected signal which will fluctuate significantly is at the difference frequency (F1-F2). This allows discrimination against any short-lived background which might be excited by two-photon or multiphoton processes. Any signal detected at the sum frequency F1+F2 will originate from contaminants of short lifetime which are able to reproduce high frequency fluctuations of emission, while the component at the difference frequency will be the sum of the desired emission from the long-lived component and that of the contaminant. There are other detection schemes that can be implemented to optimise discrimination between the different signals characteristic of label, background and scattered light and these will be familiar to those skilled in the art of signal processing.

Although the above is set out in terms of light sources modulated sinusoidally, it is equally applicable to other modulation schemes. For example, if the signals are modulated as patterns, pulses or square waves, then a desired signal will be recoverable by appropriate manipulation of a resulting detected luminescence. In a simple case where an excitation requires two different wavelengths but where neither wavelength alone is able to excite the species (e.g. a sequential process proceeding via an intermediate state), excitation is a logical AND of the modulation patterns of the two wavelengths. Unwanted signals can be detected and subtracted by simple logical manipulations of the detected emission gated by the modulation patterns driving the light sources. These alternative modulation schemes are useful insofar as they exploit the multiplicative nature of two-photon or multiphoton processes to achieve detection of luminescence with minimal interference.

Possible modulation schemes other than simple modulation of intensity at fixed frequencies (such as frequency or phase modulation of the intensity-modulating signal) may also be used.

Detection at harmonics of the modulation wave form is appropriate to upconversion media excited by multiphoton absorption and is particularly useful where relatively high power density is needed for efficient excitation. Under these conditions, it is quite possible that Anti-Stokes fluorescence or upconversion excitation of background luminescence could be seen as an interfering signal. Long-lived species such as lanthanide chelates and cryptates and complexes of, for example, ruthenium osmium, rhenium etc. are potentially useful as labels excited by riultiphoton means and have long-lived emission relative to most sources of background but require high power density for efficient excitation. Labels such as these are well suited to the proposed excitation and detection schemes. Such labels typically either have strong charge-transfer absorption bands between metal and ligand or utilise efficient intramolecular energy transfer from organic ligands to the bound metal ion.

The invention claimed is:

1. A method of detecting or quantifying an analyte by means of luminescence assay based on detection of transfer of energy between an energy donor species and an energy acceptor species as an acceptor of said energy, in which
    (i) the energy donor species is an upconversion medium that affects a transition to an excited state by absorption of electromagnetic radiation having an energy less than that of said transition and is provided as a solid phase having a surface or is immobilized in a solid phase having a surface or is immobilized on a surface of a solid phase and
    (ii) said acceptor species when bound to the surface of said solid phase in proximity to the energy donor species being excited by energy transfer from the said excited state of the donor species, the method comprising the steps of
    (a) combining a sample potentially containing the analyte with the energy donor species and the acceptor species or a precursor thereof that is converted by the analyte to the acceptor species,
    (b) irradiating said donor species with said electromagnetic radiation to excite the donor species to its said excited state for said energy transfer between the excited donor species and acceptor species bound to the surface, said analyte being one which if present either causes the acceptor species to bind to the surface in said proximity to the donor species or causes displacement of said bound acceptor species from said proximity thereby resulting in change in the excitation condition of at least one of the donor species and acceptor, species; and
    (c) detecting luminescence in at least one spectral region of the emission of said donor species or of said acceptor if said acceptor is luminescent, provided that the excitation of such a luminescent acceptor to a luminescent state emitting in said spectral region of the emission of the acceptor does not occur by absorption of a single quantum of the radiation used to excite the donor species.

2. A method as claimed in claim 1 wherein said up-conversion medium is excited by simultaneous absorption of two or more photons of the same or different energy.

3. A method as claimed in claim 1 wherein said up-conversion medium is excited by sequential absorption of two or more photons of the same or different energy.

4. A method as claimed in claim 1 wherein said up-conversion medium is an up-conversion phosphor that absorbs long wavelength radiation and emits light at shorter wavelength.

5. A method as claimed in claim 1 wherein said up-conversion medium is an electron-trapping phosphor.

6. A method as claimed in claim 1 wherein said up-conversion medium provides an up-conversion process based on the excitation of lanthanide ions in an inorganic matrix.

7. A method as claimed in claim 1 wherein said solid phase is a glassy matrix.

8. A method as claimed in claim 1 wherein said solid phase is a crystalline matrix.

9. A method as claimed in claim 1 wherein said solid phase is an organic or inorganic polymer.

10. A method as claimed in claim 1 wherein said analyte causes a change in said proximity between said energy donor species and said energy acceptor species.

11. A method as claimed in claim 1 wherein said surface of said solid phase has bound thereto recognition ligands selected from the group consisting of antibodies, lectins oligonucleotides, nucleic acids, biotin, streptavidin and avidin.

12. A method as claimed in claim 1 wherein said energy donor species emits light in two or more luminescence emission peaks that differ in efficiency of energy transfer to said energy acceptor species and wherein measurements of emission at wavelengths characteristic of at least two such peaks are made.

13. A method as claimed in claim 1 wherein the solid phase is provided with a continuous, discontinuous or partial metallic coating for enhancing transfer of energy from the upconversion medium to the acceptor species.

14. A method as claimed in claim 13 wherein the solid phase has bound thereto recognition ligands selected from the group consisting of antibodies, lectins oligonucleotides, nucleic acids, biotin, streptavidin and avidin bound to said metallic coating.

15. A method as claimed in claim 13 wherein the metallic coating is discontinuous and recognition ligands selected from the group consisting of antibodies, lectins oligonucleotides, nucleic acids, biotin, streptavidin and avidin are bonded to the solid phase at discontinuities in the metallic coating.

16. A method as claimed in claim 1 wherein said transfer of energy from said energy donor to said energy acceptor is detected by quenching of emission of said energy donor species or by sensitised emission of said energy acceptor species.

17. A method as claimed in claim 1 wherein said transfer of energy from said energy donor species to said energy acceptor species is detected by a change in luminescence decay rate of said energy donor species.

18. A method as claimed in claim 1 wherein said analyte mediates formation or dissociation of a bound complex between said energy donor species and said energy acceptor species.

19. A method as claimed in claim 1 wherein said analyte catalysts formation or cleavage of a linkage between said energy donor species and said energy acceptor species.

20. A method as claimed in claim 1 wherein said analyte interacts with said energy acceptor species or said precursor thereto causing a change in colour thereof or a change in fluorescence efficiency thereof.

21. A method as claimed in claim 1 wherein the upconversion medium comprises trivalent praseodymium as dopant.

22. A method as claimed in claim 1 wherein the upconversion medium comprises trivalent thulium as dopant.

23. A method as claimed in claim 1 wherein the upconversion medium comprises trivalent erbium as dopant.

24. A method as claimed in claim 1 wherein the upconversion medium incorporates trivalent ytterbium as a sensitising agent.

25. A method as claimed in claim 1 wherein the upconversion medium comprises a ytterbium-sensitised, erbium-dope system.

26. A method as claimed in claim 1 wherein the upconversion medium comprises a ytterbium-sensitised thulium-dope system.

* * * * *